United States Patent
Masuda et al.

(10) Patent No.: US 9,820,947 B2
(45) Date of Patent: Nov. 21, 2017

(54) METHOD OF MANUFACTURING ENTERIC SEAMLESS SOFT CAPSULE

(71) Applicant: FUJI CAPSULE CO., LTD., Shizuoka (JP)

(72) Inventors: Koji Masuda, Shizuoka (JP); Naoki Nishimura, Shizuoka (JP); Akihiko Hayano, Shizuoka (JP); Yoshiyuki Shimokawa, Shizuoka (JP); Kenji Kato, Shizuoka (JP)

(73) Assignee: FUJI CAPSULE CO., LTD., Shizuoka (JP)

( * ) Notice: Subject to any disclaimer, the term of this patent is extended or adjusted under 35 U.S.C. 154(b) by 0 days.

(21) Appl. No.: 15/516,728

(22) PCT Filed: Oct. 6, 2015

(86) PCT No.: PCT/JP2015/005081
§ 371 (c)(1),
(2) Date: Apr. 4, 2017

(87) PCT Pub. No.: WO2016/056229
PCT Pub. Date: Apr. 14, 2016

(65) Prior Publication Data
US 2017/0296474 A1    Oct. 19, 2017

(30) Foreign Application Priority Data

Oct. 6, 2014 (JP) .................................. 2014-205994

(51) Int. Cl.
*A61K 9/50* (2006.01)
*A61K 9/48* (2006.01)
*A61K 31/202* (2006.01)

(52) U.S. Cl.
CPC .......... *A61K 9/4833* (2013.01); *A61K 9/4825* (2013.01); *A61K 9/4866* (2013.01); *A61K 31/202* (2013.01)

(58) Field of Classification Search
CPC ............................ A61K 9/4833; A61K 9/4825
See application file for complete search history.

(56) References Cited

U.S. PATENT DOCUMENTS

| | | | | |
|---|---|---|---|---|
| 5,254,294 A * | 10/1993 | Wunderlich | ............. | A61J 3/07 264/4 |
| 6,410,050 B1 * | 6/2002 | Yang | .................... | A61K 9/4816 424/400 |
| 7,041,315 B2 * | 5/2006 | Scott | .................... | A61K 8/0216 424/451 |
| 7,112,292 B2 * | 9/2006 | Nakajima | ................. | A61J 3/07 264/4 |
| 7,309,499 B2 * | 12/2007 | Yang | .................... | A61K 9/4816 424/451 |

FOREIGN PATENT DOCUMENTS

| | | |
|---|---|---|
| JP | 58-172313 A | 10/1983 |
| JP | 2006-505542 | 2/2006 |
| JP | 2006-129715 A | 5/2006 |
| JP | 2009-521269 A | 6/2009 |
| JP | 2009-185022 A | 8/2009 |
| JP | 2010-047548 | 3/2010 |
| WO | 2010/146845 A1 | 12/2010 |
| WO | 2013/145379 A1 | 10/2013 |

OTHER PUBLICATIONS

International Preliminary Report on Patentability [WIPO], PCT/JP2015/005081 dated Apr. 20, 2017.

* cited by examiner

*Primary Examiner* — Kara B Boyle
(74) *Attorney, Agent, or Firm* — Edwin S. Flores; Daniel J. Chalker; Chalker Flores, LLP

(57) ABSTRACT

An object is to provide a method of manufacturing a seamless soft capsule that is enteric and excellent in formulation properties. An enteric seamless soft capsule is manufactured by the following steps (a) and (b): (a) preparing an enteric capsule shell liquid comprising gelatin and low methoxy pectin having a degree of esterification of 0 to 40% and a degree of amidation of 0 to 25%, the enteric capsule shell liquid having a viscosity at 50° C. of 60 to 127 mPa·s; and (b) encapsulating capsule fills with the enteric capsule shell liquid prepared in the step (a) by dripping. Preferably, the jelly strength of the gelatin is 180 to 330 Bloom, an aqueous solution of the low methoxy pectin at a concentration of 2 mass % has a viscosity at 35° C. of 8 to 15 mPa·s, and the enteric capsule shell liquid comprises 10 to 20 parts by mass of the low methoxy pectin per 100 parts by mass of gelatin.

20 Claims, No Drawings

METHOD OF MANUFACTURING ENTERIC SEAMLESS SOFT CAPSULE

CROSS-REFERENCE TO RELATED APPLICATIONS

This application is the National Stage of International Application No. PCT/JP2015/005081, filed on Oct. 6, 2015 claiming the priority of JP 2014-205994, filed on Oct. 6, 2014, the content of each of which is incorporated by reference herein.

TECHNICAL FIELD

The present invention relates to a method of manufacturing an enteric seamless soft capsule, and more particularly to a method of manufacturing an enteric seamless soft capsule, comprising the following steps (a) and (b): (a) preparing an enteric capsule shell liquid comprising gelatin and low methoxy pectin having a degree of esterification of 0 to 40% and a degree of amidation of to 25%, the enteric capsule shell liquid having a viscosity at 50° C. of 60 to 127 mPa·s; and (b) encapsulating capsule fills with the enteric capsule shell liquid prepared in the step (a) by dripping.

BACKGROUND ART

A variety of conventional capsules containing various active ingredients have been reported. Widely used materials of shells of these capsules include gelatin and agar. Since shells made of materials such as gelatin and agar disintegrate in the acidic environment of the stomach, it was not possible to use acid-labile substances as active ingredients.

Enteric capsules have been recently developed for this reason. Enteric capsules are capsules whose shells have acid resistance, therefore do not disintegrate in the stomach, but disintegrate in the intestines to release the capsule fills. These enteric capsules are used not only to encapsulate acid-labile substances as active ingredients, but also to encapsulate substances to be released slowly for effects sustained for a long period of time and substances that cause bad breath and flavor reversion when digested in the stomach, such as garlic and a fish oil.

Methods of manufacturing enteric capsules proposed so far include a method comprising (a) preparing a solution comprising a film-forming, water-soluble polymer and an acid-insoluble polymer and mixing with appropriate plasticizers to form a gel mass; (b) casting the gel mass into films or ribbons using heat-controlled drums or surfaces; and (c) forming a soft capsule using rotary die technology (see Patent Document 1), and a method of manufacturing an enteric, sustained-release soft capsule, comprising manufacturing a soft capsule material mixture obtained by homogeneously mixing and kneading gelatin, polyol as a plasticizer, an alkali metal salt, water, and a polysaccharide such as carrageenan, agar, or locust bean gum at a concentration of 6 to 40% by mass; and encapsulating at least one selected from garlic, a fish oil, propolis, an enteric bacterium, and a protein agent with the soft capsule material mixture (see Patent Document 2).

Further proposed is a method of manufacturing an enteric soft capsule, comprising a preparation step of preparing a capsule shell liquid comprising gelatin, water, a plasticizer, and 10 to 30 parts by weight of low methoxyl pectin having a degree of esterification of 20 to 40% per 100 parts by weight of gelatin; and a capsule-forming step of forming a soft capsule in which fill materials are packed into a capsule shell formed from the capsule shell liquid with a rotary die capsule-forming apparatus; wherein the capsule shell liquid comprises no salts comprising a polyvalent metal ion that gelates low methoxyl pectin and the method comprises no step of immersing the formed soft capsule in a gelation solution comprising the polyvalent metal ion (see Patent Document 3).

PRIOR ART DOCUMENTS

Patent Documents

Patent Document 1: Japanese unexamined Patent Application Publication (Translation of PCT Application) No. 2006-505542
Patent Document 2: Japanese unexamined Patent Application Publication No. 2009-185022
Patent Document 3: Japanese unexamined Patent Application Publication No. 2010-047548

SUMMARY OF THE INVENTION

Object to be Solved by the Invention

An object of the present invention is to provide a method of manufacturing a seamless soft capsule that is enteric and excellent in formulation properties.

Means to Solve the Object

The present inventors focused on the degree of amidation and the degree of esterification of pectin used in a capsule shell and the viscosity of the shell liquid in the manufacturing of enteric seamless soft capsules. The present inventors found that seamless soft capsules that are enteric and excellent in formulation properties can be manufactured by using gelatin and low methoxy pectin having a degree of esterification of 0 to 40% and a degree of amidation of 0 to 25% as capsule shell materials and making the viscosity of the shell liquid at 50° C. 60 to 127 mPa·s, thereby completing the present invention.

Accordingly, the present invention is as disclosed below.
(1) A method of manufacturing an enteric seamless soft capsule, comprising the following steps (a) and (b): (a) preparing an enteric capsule shell liquid comprising gelatin and low methoxy pectin having a degree of esterification of 0 to 40% and a degree of amidation of 0 to 25%, the enteric capsule shell liquid having a viscosity at 50° C. of 60 to 127 mPa·s; and (b) encapsulating capsule fills with the enteric capsule shell liquid prepared in the step (a) by dripping.
(2) The method of manufacturing an enteric seamless soft capsule according to (1) above, wherein a jelly strength of the gelatin is 180 to 330 Bloom.
(3) The method of manufacturing an enteric seamless soft capsule according to (1) or (2) above, wherein an aqueous solution of the low methoxy pectin at a concentration of 2 mass % has a viscosity at 35° C. of 8 to 15 mPa·s.
(4) The method of manufacturing an enteric seamless soft capsule according to any one of (1) to (3) above, wherein the enteric capsule shell liquid comprises 10 to 20 parts by mass of the low methoxy pectin per 100 parts by mass of the gelatin.
(5) The method of manufacturing an enteric seamless soft capsule according to any one of (1) to (4) above, wherein the enteric capsule shell liquid has a viscosity at 50° C. of 70 to 110 mPa·s.

(6) The method of manufacturing an enteric seamless soft capsule according to any one of (1) to (5) above, wherein the low methoxy pectin has a degree of amidation of 5 to 25%.
(7) The method of manufacturing an enteric seamless soft capsule according to any one of (1) to (6) above, wherein the low methoxy pectin is dispersed in glycerin and subsequently dissolved in hot water, then gelatin is added and dissolved, and the mixture is filtered and degassed with standing.
(8) The method of manufacturing an enteric seamless soft capsule according to any one of (1) to (7) above, wherein the encapsulating is performed such that an enteric capsule shell rate is 9 to 30 mass %.

Effects of the Invention

Enteric seamless soft capsules manufactured by the present invention are enteric and excellent in formulation properties. Therefore, they can be produced easily and encapsulate fill materials containing an acid-labile substance. In addition, they can prevent bad breath and flavor reversion after administering fill materials containing a substance that causes bad breath or flavor reversion when digested in the stomach, such as garlic and a fish oil, encapsulated therein.

MODE OF CARRYING OUT THE INVENTION

A method of manufacturing an enteric seamless soft capsule according to the present invention is not particularly limited as long as it is a method of manufacturing an enteric seamless soft capsule, comprising the following steps (a) and (b): (a) preparing an enteric capsule shell liquid comprising gelatin and low methoxy pectin having a degree of esterification of 0 to 40% and a degree of amidation of 0 to 25%, the enteric capsule shell liquid having a viscosity at 50° C. of 60 to 127 mPa·s; and (b) encapsulating capsule fills with the enteric capsule shell liquid prepared in the step (a) by dripping. "Enteric" refers to the property of being dissolved in intestines, but not dissolved in the stomach.

Gelatin in the present invention is not particularly limited, but examples include gelatin having a jelly strength of 180 to 330 Bloom, and preferably 250 to 320 Bloom. Moreover, mixtures of 2 or more gelatins different in jelly strength can be used.

In the present invention, low methoxy pectin (LM pectin) refers to pectin having a degree of esterification (DE) of less than 50% and such a degree of esterification is 0 to 40% and may be 3 to 38%, 3 to 12%, or 22 to 35%, as long as the viscosity of the enteric capsule shell liquid at 50° C. is 60 to 127 mPa·s. The degree of esterification means percentage of methyl esterified galacturonic acid to total galacturonic acid and is the value (%) calculated by dividing the number of methyl esterified galacturonic acid by the number of total galacturonic acid and multiplying the obtained value by 100.

Examples of the viscosity of an aqueous solution of the low methoxy pectin at a concentration of 2 mass % at 35° C. include 8 to 15 mPa·s and preferably 9 to 14 mPa·s.

In the present invention, degree of amidation (DA) means percentage of amidated galacturonic acid to total galacturonic acid and is the value (%) calculated by dividing the number of amidated galacturonic acid by the number of total galacturonic acid and multiplying the obtained value by 100. The degree of amidation of the aforementioned low methoxy pectin is 0 to 25% and may be 0, 5 to 25%, or 6 to 23% as long as the enteric capsule shell liquid has a viscosity at 50° C. of 60-127 mPa·s.

A method of preparing an enteric capsule shell liquid according to the present invention is not particularly limited but examples include a method comprising dissolving low methoxy pectin having degree of esterification of 0 to 40% and a degree of amidation of 0 to 25% in water then adding gelatin to the mixture and dissolving the gelatin. In view of quality control such as securing of the homogeneity of the shell liquid, the prevention of weakening of capsule shells, and the prevention of deformation and poor adhesiveness of capsules, it is preferred to dissolve the aforementioned low methoxy pectin in hot water after dispersing it in a plasticizer such as glycerin; to filter the prepared enteric capsule shell liquid through a mesh with 0.5 mm or smaller aperture, and preferably 0.3 mm or smaller; and to further degas the shell liquid with standing till at least apparent forms are disappeared when the shell liquid is liquid.

In the present invention, example of a method of encapsulating capsule fills by dripping include a method comprising discharging various liquid flows into a solidification liquid or a gas from a concentric multiplex nozzle such as a double nozzle or a triple nozzle and encapsulating capsule fills in a capsule shell liquid. Such a method can be conducted using a commercially available dripping seamless soft capsule producing apparatus and produce seamless capsules, which have no seams.

In the present invention, capsule fills are not particularly limited and can be a solid or a liquid and examples include a pharmaceutical ingredient, a supplement ingredient, and a health food ingredient. Specific examples include a substance that causes bad breath or flavor reversion when digested in the stomach such as a fish oil, garlic, vitamin B1, or so-called egg-yolk oil (a traditional health food material that is a brown to black liquid obtained by heating egg yolk over a low flame with stirring in an iron pan or the like for a long time); an acid-labile enteric bacterium such as a lactic acid bacterium and a bifidobacterium; an ingredient stimulating to the stomach such as a red pepper material or capsaicin; a chalybeate such as ferrous fumarate or dried ferrous sulfate: and an agent desired to be released slowly to have an effect sustained for a long period of time such as an antifebrile, a pain-killer, an antiphlogistic, an antitumor agent, or an antimicrobial agent.

Besides the aforementioned ingredients, the aforementioned capsule fills can contain, as needed, an oil or fat such as hydrogenated oil, medium chain triglyceride (MCT), EPA, DHA, shark liver oil, or cod-liver oil; an additive that can be used to adjust the surface activity such as lecithin, polyglycerol ester of fatty acid, or alcohol; buffer; water; a gelling agent such as gelatin or carrageenan; a pH regulator; porous fine particle powder such as gas phase process silica; a tasting agent such as a sweetener; a flavor; a solubilizer; a viscosity modifier; an antioxidant represented by vitamin E, BHT, BHA.

The content of the low methoxy pectin relative to gelatin in the enteric capsule shell liquid of the present invention is not particularly limited, but the content of the low methoxy pectin is preferably 10 to 20 parts by mass, more preferably 11 to 18 parts by mass per 100 parts by mass of the gelatin.

In the present invention, encapsulation of capsule fills is preferably conducted such that the enteric capsule shell rate of the produced enteric seamless soft capsules is 9 to 30 mass % and more preferably such that the enteric capsule shell rate is 10 to 20 mass %. Herein, the shell rate refers to the mass percentage of the shell in the whole capsule.

The enteric capsule shell liquid in the present invention can contain, as needed, a plasticizer such as glycerin, a PH regulator such as sodium phosphate, a chelating agent such as trisodium citrate or sodium metaphosphate, a gelling enhancer such as calcium lactate or potassium chloride, a surfactant such as polyglycerol ester of fatty acid or lecithin, a sweetener, a flavor, a preservative, or a colorant.

The viscosity of the aforementioned enteric capsule shell liquid is a viscosity at 50° C. of 60 to 127 mPa·s and preferable examples include 70 to 100 mPa·s. The viscosity of the enteric capsule shell liquid can be determined by using a commercially available viscometer, such as "BII Viscometer" (manufactured by Toki Sangyo Co., Ltd.).

EXAMPLES

Example 1

[Administration Test]
(Production of Seamless Soft Capsule)

15 parts by mass of pectin (DE7, DA0) was dispersed in 20 parts by mass of glycerin and dissolved in 750 parts by mass of hot water (80° C.). 85 parts by mass of gelatin (300 Bloom) was further added to the solution and dissolved at 70° C. The solution was filtered through 100 mesh (aperture 0.15 mm) and subsequently degassed with standing to prepare a capsule shell liquid (1) according to the present invention. The viscosity of the shell liquid (50° C.) as measured with a BII viscometer (manufactured by Toki Sangyo Co., Ltd.) was 85 mPa·s.

Moreover, 10 parts by mass of pectin (DE7, DA0) was dispersed in 5 parts by mass of glycerin and dissolved in 950 parts by mass of hot water (80° C.). 85 parts by mass of gelatin (200 Bloom) was further added to the solution and dissolved at 70° C. The solution was filtered through 100 mesh (aperture 0.15 mm) and subsequently degassed with standing to prepare a capsule shell liquid (2) according to the present invention. The viscosity of the shell liquid (50° C.) as measured with a BII viscometer (manufactured by Toki Sangyo Co., Ltd.) was 70 mPa·s.

Furthermore, a control shell liquid was prepared by dissolving 100 parts by mass of gelatin (200 Bloom) and 30 parts by mass of glycerin in 750 parts by mass of hot water (70° C.), filtering the solution through 100 mesh, and subsequently degassing the filtrate with standing. The viscosity of the shell liquid (50° C.) as measured with a BII viscometer (manufactured by Toki Sangyo Co., Ltd.) was 90 mPa·s.

Then, by a dripping seamless soft capsule manufacturing apparatus (manufactured by Fuji Capsule Co., Ltd.) with a double nozzle, 80 mg of capsule fills (a fish oil containing DHA and EPA) was encapsulated with the capsule shell liquid (1) according to the present invention, the capsule shell liquid (2) according to the present invention, or the control shell liquid described above. The resulting capsules were subsequently dried at 30° C. and 25% RH for 12 hours to manufacture seamless soft capsules. A medium chain triglyceride (MCT: COCONARD MT: manufactured by Kao Corporation) at 10° C. was used as a cooling oil.

(Result)

Seamless soft capsules manufactured using the capsule shell liquid (1) according to the present invention, seamless soft capsules manufactured using the capsule shell liquid (2) according to the present invention, and seamlessness software capsules manufactured using the control shell liquid were administered and the smell of the expiration was examined 30 minutes later. As a result, no fishy smell derived from fish was detected after the administration of the seamless soft capsules manufactured using the capsule shell liquid (1) according to the present invention or the capsule shell liquid (2) according to the present invention, but a fishy smell derived from fish was detected after the administration of the seamless soft capsules manufactured using the control shell liquid.

Example 2

[Formulation and Enteric Properties Test]
(Production of Seamless Soft Capsule)

15 parts by mass of each type of pectin set forth in Table 1 below was dispersed in 20 parts by mass of glycerin and dissolved in 750 parts by mass of hot water (80° C.), 85 parts by mass of gelatin (300 Bloom) was further added and dissolved at 70° C. The mixture was filtered through 80 mesh (aperture 0.18 mm) and subsequently degassed with standing to prepare a capsule shell liquid.

TABLE 1

|  | DE | DA | Viscosity at 35° C. | Viscosity at 50° C. | Viscosity of shell liquid |
| --- | --- | --- | --- | --- | --- |
| Pectin-1 | 31-38 | 12-18 | 14 | 11 | 125 |
| Pectin-2 | 26-34 | 16-19 | 13 | 11 | 120 |
| Pectin-3 | 22-27 | 20-23 | 11 | 10 | 75 |
| Pectin-4 | 30-35 | 6-12 | 13 | 11 | 100 |
| Pectin-5 | 3-12 | 0 | 9 | 7 | 85 |
| Pectin-6 | 33-38 | 0 | 16 | 11 | 130 |

In the table, DE indicates the degree of esterification (%) of each type of pectin, DA indicates the degree of amidation (%) of each type of pectin, Viscosity at 35° C. or Viscosity at 50° C. indicate the viscosity (mPa·s) of an aqueous solution of each type of pectin at a concentration of 2 mass % at 35° C. or 50° C. as measured with a BII Viscometer (manufactured by Toki Sangyo Co., Ltd.), and Viscosity of shell liquid indicates the viscosity (mPa·s) of the capsule shell liquid (50° C.) prepared by the method described above with dissolving each type of pectin as measured with the aforementioned viscometer.

Then, by a dripping seamless soft capsule manufacturing apparatus (manufactured by Fuji Capsule Co., Ltd.), 100 mg of MCT (COCONARD MT: manufactured by Kao Corporation) was encapsulated, as capsule fills, with each of the aforementioned capsule shell liquids. The resulting capsules were subsequently dried at 30° C. and 25% RH for 12 hours to manufacture seamless soft capsules. Seamless soft capsules manufactured with shell liquids containing Pectin-1 to Pectin-5 were respectively designated as Example Products 1 to 5 and a seamless soft capsule manufactured with Pectin 6 were designated as Comparison Product. The shell rate of the obtained seamless soft capsules was 18 mass %.

The obtained seamless soft capsules were evaluated for their formulation properties and enteric properties. For the evaluation of formulation properties, the shape of the capsule at the time of dropping to MCT at 10° C. was examined as the formability and rated into the 4 grades of excellent, good, acceptable, and unacceptable.

For evaluation of enteric properties, the disintegration tests described below were conducted and results of the observation after 120 minutes of the disintegration test in 1st Fluid (37° C.) were rated as ○ when there was no rupturing and x when there was rupturing; and results of the observation after 30 minutes of the disintegration test in 2nd Fluid were rated as ○ when all capsules were disintegrated and x when not all capsules were disintegrated.

The disintegration tests of the manufactured seamless soft capsules were conducted by methods modified from the methods described in literature (Guidebook to The Japanese Pharmacopoeia 16th edition, Tokyo Hirokawa Shoten, publication B589 (2011)). The disintegration tester NT-40H (manufactured by Toyama Sangyo Co., Ltd.) was used. A test using the reagent "1st Fluid for disintegration test/1st Fluid for dissolution test" (pH 1.2) manufactured by Kanto Chemical Co., Inc. and a test using the reagent "2nd Fluid for disintegration test" (pH 6.8) manufactured by Kanto Chemical Co., Inc. were conducted for 18 capsules each without a disk. Capsules were considered disintegrated when they were broken or their shells were ruptured or damaged.

(Result)

The results of the examination on formulation properties and enteric properties are shown in Table 2. As shown in Table 2, all of Example products 1 to 5 had good formulation properties. As to enteric properties, Example Products 1 to 5 exhibited no disintegration for all 18 seamless soft capsules after 120 minutes of the disintegration test in 1st Fluid and exhibited disintegration from after 5 minutes of the test in 2nd Fluid for disintegration test using new capsule samples and all 18 seamless soft capsules were disintegrated after 30 minutes of the test.

Thus, it was revealed that seamless soft capsules excellent in formulation properties and enteric properties can be produced by producing seamless soft capsules by dripping using an enteric capsule shell liquid comprising gelatin and low methoxy pectin having a degree of esterification of 0 to 40% and a degree of amidation of 0 to 25%, the enteric capsule shell liquid having a viscosity at 50° C. of 60 to 127 mPa·s.

TABLE 2

| | | Evaluation of formulation properties | Evaluation of enteric properties | |
|---|---|---|---|---|
| | Pectin type | Formability | 1st Fluid | 2nd Fluid |
| Example Product 1 | Pectin-1 | Good | ○ | ○ |
| Example Product 2 | Pectin-2 | Good | ○ | ○ |
| Example Product 3 | Pectin-3 | Excellent | ○ | ○ |
| Example Product 4 | Pectin-4 | Excellent | ○ | ○ |
| Example Product 5 | Pectin-5 | Good | ○ | ○ |
| Comparison Product | Pectin-6 | Acceptable | x | — |

INDUSTRIAL APPLICABILITY

The enteric seamless soft capsules manufactured by the present invention are excellent in enteric properties and formulation properties and available in the fields of pharmaceuticals, supplements, and health food.

The invention claimed is:

1. A method of manufacturing an enteric seamless soft capsule, comprising the following steps (a) and (b):
   (a) preparing an enteric capsule shell liquid comprising gelatin and low methoxy pectin having a degree of esterification of 0 to 40% and a degree of amidation of 0 to 25%, the enteric capsule shell liquid having a viscosity at 50° C. of 60 to 127 mPa·s; and
   (b) encapsulating capsule fills with the enteric capsule shell liquid prepared in the step (a) by dripping.

2. The method of manufacturing an enteric seamless soft capsule according to claim 1, wherein a jelly strength of the gelatin is 180 to 330 Bloom.

3. The method of manufacturing an enteric seamless soft capsule according to claim 1, wherein an aqueous solution of the low methoxy pectin at a concentration of 2 mass % has a viscosity at 35° C. of 8 to 15 mPa·s.

4. The method of manufacturing an enteric seamless soft capsule according to claim 1, wherein the enteric capsule shell liquid comprises 10 to 20 parts by mass of the low methoxy pectin per 100 parts by mass of the gelatin.

5. The method of manufacturing an enteric seamless soft capsule according to claim 1, wherein the enteric capsule shell liquid has a viscosity at 50° C. of 70 to 110 mPa·s.

6. The method of manufacturing an enteric seamless soft capsule according to claim 1, wherein the low methoxy pectin has a degree of amidation of 5 to 25%.

7. The method of manufacturing an enteric seamless soft capsule according to claim 1, wherein the low methoxy pectin is dispersed in glycerin and subsequently dissolved in hot water, then gelatin is added and dissolved, and the mixture is filtered and degassed with standing.

8. The method of manufacturing an enteric seamless soft capsule according to claim 1, wherein the encapsulating is performed such that an enteric capsule shell rate is 9 to 30 mass %.

9. The method of manufacturing an enteric seamless soft capsule according to claim 2, wherein an aqueous solution of the low methoxy pectin at a concentration of 2 mass % has a viscosity at 35° C. of 8 to 15 mPa·s.

10. The method of manufacturing an enteric seamless soft capsule according to claim 2, wherein the enteric capsule shell liquid comprises 10 to 20 parts by mass of the low methoxy pectin per 100 parts by mass of the gelatin.

11. The method of manufacturing an enteric seamless soft capsule according to claim 3, wherein the enteric capsule shell liquid comprises 10 to 20 parts by mass of the low methoxy pectin per 100 parts by mass of the gelatin.

12. The method of manufacturing an enteric seamless soft capsule according to claim 9, wherein the enteric capsule shell liquid comprises 10 to 20 parts by mass of the low methoxy pectin per 100 parts by mass of the gelatin.

13. The method of manufacturing an enteric seamless soft capsule according to claim 2, wherein the enteric capsule shell liquid has a viscosity at 50° C. of 70 to 110 mPa·s.

14. The method of manufacturing an enteric seamless soft capsule according to claim 3, wherein the enteric capsule shell liquid has a viscosity at 50° C. of 70 to 110 mPa·s.

15. The method of manufacturing an enteric seamless soft capsule according to claim 4, wherein the enteric capsule shell liquid has a viscosity at 50° C. of 70 to 110 mPa·s.

16. The method of manufacturing an enteric seamless soft capsule according to claim 9, wherein the enteric capsule shell liquid has a viscosity at 50° C. of 70 to 110 mPa·s.

17. The method of manufacturing an enteric seamless soft capsule according to claim 10, wherein the enteric capsule shell liquid has a viscosity at 50° C. of 70 to 110 mPa·s.

18. The method of manufacturing an enteric seamless soft capsule according to claim 11, wherein the enteric capsule shell liquid has a viscosity at 50° C. of 70 to 110 mPa·s.

19. The method of manufacturing an enteric seamless soft capsule according to claim 12, wherein the enteric capsule shell liquid has a viscosity at 50° C. of 70 to 110 mPa·s.

20. The method of manufacturing an enteric seamless soft capsule according to claim 2, wherein the low methoxy pectin has a degree of amidation of 5 to 25%.

* * * * *